(12) United States Patent
Kalyankar et al.

(10) Patent No.: US 9,177,107 B2
(45) Date of Patent: Nov. 3, 2015

(54) RECIPIENT VERIFICATION SYSTEM WITH PERMANENT IDENTIFIER HAVING EMBEDDED MACHINE READABLE CODE VERIFICATION AND METHODS OF USE, INCLUDING RECIPIENT IDENTIFICATION

(71) Applicant: Typenex Medical, LLC, Chicago, IL (US)

(72) Inventors: Varsha Kalyankar, Chicago, IL (US); Scott Leece, Chicago, IL (US); Keith Gavin, Evergreen Park, IL (US); Luke Westra, Chicago, IL (US)

(73) Assignee: Typenex Medical, LLC, Chicago, IL (US)

( * ) Notice: Subject to any disclaimer, the term of this patent is extended or adjusted under 35 U.S.C. 154(b) by 0 days.

(21) Appl. No.: 14/180,481

(22) Filed: Feb. 14, 2014

(65) Prior Publication Data

US 2014/0224873 A1    Aug. 14, 2014

Related U.S. Application Data

(60) Provisional application No. 61/764,762, filed on Feb. 14, 2013.

(51) Int. Cl.
  *G06F 17/00*    (2006.01)
  *G06K 7/10*    (2006.01)
  *G06F 19/00*    (2011.01)
  *G09F 3/00*    (2006.01)

(52) U.S. Cl.
  CPC ............. *G06F 19/323* (2013.01); *G09F 3/005* (2013.01)

(58) Field of Classification Search
  CPC ......... G09F 3/005; G09F 3/10; G09F 3/0297; A61B 5/117; G08B 21/22; Y10S 283/90; G06F 19/322; G06F 19/3487; G06Q 10/00; G06Q 50/24
  USPC ............................. 235/375, 462.01; 705/2, 3
  See application file for complete search history.

(56) References Cited

U.S. PATENT DOCUMENTS

| | | |
|---|---|---|
| 3,106,028 A | 10/1963 | Baumgartner |
| 3,323,208 A | 6/1967 | Hurley |
| 3,416,200 A | 12/1968 | Daddona, Jr. |
| 3,586,220 A | 6/1971 | Reinsberg |
| 3,645,023 A | 2/1972 | Larson |
| 3,656,247 A | 4/1972 | Bushnell et al. |
| 3,660,916 A | 5/1972 | McDermott et al. |
| 3,698,383 A | 10/1972 | Baucom |
| 3,715,570 A | 2/1973 | Weichselbaum et al. |
| 3,744,104 A | 7/1973 | Ford |
| 3,744,691 A | 7/1973 | Shears |
| 3,751,835 A | 8/1973 | Smith |
| 3,965,589 A | 6/1976 | McDermott |
| 4,164,320 A | 8/1979 | Irazoqui et al. |

(Continued)

*Primary Examiner* — Tuyen K Vo
(74) *Attorney, Agent, or Firm* — Dicke, Billig & Czaja, PLLC

(57) ABSTRACT

A recipient verification system including a band and at least one label intended to be removed from connection with the band during use. The band displays a permanent band identifier, and the at least one label displays a removable band identifier. The band identifiers each include an identical human readable code. The removable band identifier further includes a machine readable code embodying information identical to, and limited to, the human readable code. The permanent band identifier includes a machine readable code embodying information identical to the human readable code and a verification code.

20 Claims, 4 Drawing Sheets

(56) References Cited

U.S. PATENT DOCUMENTS

| | | | | |
|---|---|---|---|---|
| 4,226,036 | A | 10/1980 | Krug | |
| 4,233,715 | A | 11/1980 | McDermott | |
| 4,377,047 | A | 3/1983 | Adams et al. | |
| 4,914,843 | A | 4/1990 | DeWoskin | |
| 5,002,212 | A | 3/1991 | Charleton | |
| 5,088,159 | A | 2/1992 | Lafleur | |
| 5,092,067 | A | 3/1992 | Prout | |
| 5,164,575 | A | 11/1992 | Neeley et al. | |
| 5,166,498 | A | 11/1992 | Neeley | |
| 5,226,809 | A | 7/1993 | Franco | |
| 5,283,969 | A | 2/1994 | Weiss | |
| 5,311,689 | A | 5/1994 | Lindsey | |
| 5,323,554 | A | 6/1994 | MacDonald | |
| 5,343,608 | A | 9/1994 | MacDonald | |
| 5,401,110 | A | 3/1995 | Neeley | |
| 5,423,574 | A | 6/1995 | Forte-Pathroff | |
| 5,488,846 | A | 2/1996 | Green | |
| 5,499,468 | A | 3/1996 | Henry | |
| 5,581,924 | A | 12/1996 | Peterson | |
| 5,615,504 | A | 4/1997 | Peterson et al. | |
| 5,740,623 | A | 4/1998 | Juhan et al. | |
| 5,758,443 | A | 6/1998 | Pedrazzini | |
| 5,979,941 | A | 11/1999 | Mosher, Jr. et al. | |
| 6,092,321 | A | 7/2000 | Cheng | |
| 6,255,951 | B1 | 7/2001 | De La Huerga | |
| 6,349,493 | B1 | 2/2002 | Newman et al. | |
| 6,421,920 | B1 | 7/2002 | Jensen | |
| 6,641,048 | B1 * | 11/2003 | Schintz et al. | 235/487 |
| 6,655,063 | B2 | 12/2003 | Goodin et al. | |
| 6,748,687 | B2 | 6/2004 | Riley | |
| 6,922,148 | B2 | 7/2005 | Despotis | |
| 6,948,271 | B2 | 9/2005 | Helgeson et al. | |
| 6,976,327 | B2 | 12/2005 | Goodin et al. | |
| 7,017,293 | B2 | 3/2006 | Riley | |
| 7,017,294 | B2 * | 3/2006 | Riley | 40/633 |
| 7,137,216 | B2 | 11/2006 | Ali et al. | |
| 7,188,764 | B2 | 3/2007 | Penuela | |
| 7,197,842 | B2 | 4/2007 | Ali | |
| 7,222,448 | B2 | 5/2007 | Riley | |
| 7,240,446 | B2 | 7/2007 | Bekker | |
| 7,286,055 | B2 | 10/2007 | Girvin et al. | |
| 7,481,370 | B2 | 1/2009 | Davis et al. | |
| 7,654,024 | B2 * | 2/2010 | Riley | 40/633 |
| 8,028,450 | B2 | 10/2011 | Landsman et al. | |
| 2004/0060215 | A1 * | 4/2004 | Riley | 40/633 |
| 2004/0060216 | A1 | 4/2004 | Riley | |
| 2004/0148836 | A1 | 8/2004 | Riley | |
| 2004/0244251 | A1 | 12/2004 | Riley | |
| 2005/0091896 | A1 | 5/2005 | Kotik et al. | |
| 2005/0108912 | A1 * | 5/2005 | Bekker | 40/633 |
| 2005/0184508 | A1 | 8/2005 | Verden et al. | |
| 2006/0168861 | A1 * | 8/2006 | Riley | 40/633 |
| 2006/0174527 | A1 | 8/2006 | Henley | |
| 2006/0230661 | A1 | 10/2006 | Bekker | |
| 2006/0236578 | A1 * | 10/2006 | Saint et al. | 40/633 |
| 2006/0242875 | A1 | 11/2006 | Wilson et al. | |
| 2006/0254105 | A1 | 11/2006 | Chang | |
| 2007/0028495 | A1 | 2/2007 | Kotik et al. | |
| 2007/0120358 | A1 | 5/2007 | Waggoner et al. | |
| 2007/0172291 | A1 | 7/2007 | Yokoyama | |
| 2007/0257113 | A1 * | 11/2007 | Davis et al. | 235/462.01 |
| 2008/0223929 | A1 * | 9/2008 | Togashi et al. | 235/385 |
| 2008/0301990 | A1 | 12/2008 | McDermott | |
| 2009/0212101 | A1 * | 8/2009 | Tan | 235/375 |
| 2010/0024268 | A1 | 2/2010 | Landsman et al. | |
| 2010/0258641 | A1 * | 10/2010 | Yu | 235/494 |
| 2011/0107637 | A1 | 5/2011 | Bekker | |
| 2012/0075076 | A1 * | 3/2012 | Wang | 340/10.4 |
| 2012/0180351 | A1 | 7/2012 | Kalyankar et al. | |
| 2012/0310848 | A1 * | 12/2012 | Gao et al. | 705/317 |

* cited by examiner

RECIPIENT VERIFICATION SYSTEM WITH PERMANENT IDENTIFIER HAVING EMBEDDED MACHINE READABLE CODE VERIFICATION AND METHODS OF USE, INCLUDING RECIPIENT IDENTIFICATION

CROSS REFERENCE TO RELATED APPLICATION

This Non-Provisional Patent Application claims the benefit of the filing date of U.S. Provisional Patent Application Ser. No. 61/764,762, filed Feb. 14, 2013, which is herein incorporated by reference.

BACKGROUND

The present disclosure relates to recipient verification bands and related systems, for example patient identification systems. More particularly, it relates to wearable verification bands for use in various environments, such as caregiver environments. Said verification bands provide users with various labels and labeling methods, which can be linked to the wearer of the band, and include identification information formatted to facilitate confirmation that desired protocols are followed during use. The systems described in the present disclosure are amenable for various end applications and methods for making the same.

The need to assign a unique code or other identifier to a person or thing (collectively referred to as a "recipient") and to employ the identifier in correlating articles or activities to the recipient arises in a number of contexts. For example, positive patient identification is a critical step in providing medical treatment to patients in a caregiver environment (e.g., hospital). Commonly, an identification band (e.g., a flexible plastic wristband or ankle band) is issued to the patient at the time of admission to the caregiver institution, and is worn by the patient at all times (sometimes referred to as an "admission band"). The issued identification/admission band typically displays patient-related information (e.g., printed or labeled), such as name, date of birth, etc.

In some instances, a unique patient identifier or other code is assigned to the patient and is displayed on the admission band, including, for example, a bar code or numeric/alphanumeric code. The patient identifier can alternatively be supplied on a separate band (apart from the admission band), and is used to cross-reference other caregiver-related items with the patient via, for example, an electronic data base. The unique patient identifier provides an independent, physical link between the patient and associated patient articles or caregiver activities when applied to such articles. For example, paperwork or other caregiver documents/medical charts relating to the patient may include the patient identifier. In addition, the patient identifier can be applied to specimen samples (e.g., test tubes for blood specimens) taken from the patient, or applied to therapeutic material(s) to be given to the patient. The patient identifier ensures that said items are accurately associated with the correct patient at all stages of the patient's visit with the caregiver institution. Similar recipient verification needs apart from hospital admission may be found in multiple other situations including blood transfusion, pharmaceutical administration, trauma centers, etc. In these and other environments, a lack of immediate patient identification and verification can pose significant safety risks.

To facilitate accurate transposition of the patient identifier (and possibly other patient-related information) to items apart from the band(s) worn by the patient, it is known to provide one or more labels or tags that display the same patient identifier. Alternatively, it is also known to permit a caregiver to enter the patient identifier onto the label/tag. This manual process of transferring the patient identifier from the patient to his specimens, test requests, etc. and then back to the patient is prone to error. First, if the unique patient identifier or patient information must be transcribed by hand, the potential for human error will arise. Second, the patient identifier and/or patient information must be transferred to the correct specimen/item in question. In order to avoid transcription errors, it is desirable to use these patient identification labels in combination with the unique patient identifier. Hospital admission bands are commonly supplied with a plurality of patient identifying labels. In addition, laboratory test requests often can generate multiple patient identifying labels. In all these scenarios, the companion labels with the matching patient identifier information are separate from the patient identifier attached directly to the patient. This lack of direct physical connection can lead to confusion, lost labels, and other problems.

While systems exist that address several of the problems raised above, current systems also give rise to other concerns. For example, with patient identification bands and labels incorporating a barcode-type patient identifier, caregivers are often required to retrieve or scan information in a specified fashion. More particularly, many caregiver facility protocols dictate that when electronically associating a particular patient with a particular item, activity, etc., the caregiver must scan the patient identifier barcode displayed on the band worn by the patient. While the caregiver may subsequently scan the patient identifier barcode displayed on one of the labels as part of the same activity, the barcode on the worn band must be scanned as part of the matching process. This protocol addresses a concern that a caregiver might scan only a label barcode under the assumption that this label "belongs" to the intended patient, when in fact the scanned label is associated with a different patient. While caregivers may have easier access to removed labels and thus can more quickly complete the particular activity by scanning the label barcode instead of the barcode on the worn band, scanning only the barcode on the worn band ensures that the correct barcode information for the intended patient has been received. Unfortunately, many available recipient verification systems do not provide a mechanism to confirm that this protocol has been followed. A need exists for an improved recipient verification system that addresses the above challenges.

SUMMARY

Aspects of the present disclosure relate to a recipient verification system including a band and at least one label intended to be removed from connection with the band during use. The band displays a permanent band identifier, and the at least one label displays a removable band identifier. The band identifiers each include an identical human readable code. The removable band identifier further includes a machine readable code (e.g., a barcode) embodying information identical to, and limited to, the human readable code. The permanent band identifier includes a machine readable code embodying information identical to the human readable code along with a verification code.

DETAILED DESCRIPTION

Aspects of the present disclosure relate to recipient verification systems useful in a variety of different environments. For example, the recipient verification systems of the present disclosure can be used in medical or patient-related contexts, such as with patient admission to a hospital (and related medical records, charts, items (e.g., clothing), etc.), testing or specimen drawing (e.g., X-rays, blood specimen, DNA specimen, organ donation, stem cell specimen, fertilized eggs, etc.) entirely apart from (or as part of) a hospital stay, blood banks, pharmacies (e.g., custom chemotherapy drugs, nuclear pharmacy, labor and delivery, etc.), or other instances in which patient identification is needed. Other applications are equally appropriate, such as police or security situations in which a number of individuals must be quickly processed on-site, ticketing applications, etc. Thus, while several of the examples described below mention patient identification, as well as hospital admission, the systems of the present disclosure are in no way limited.

Figure 1A:
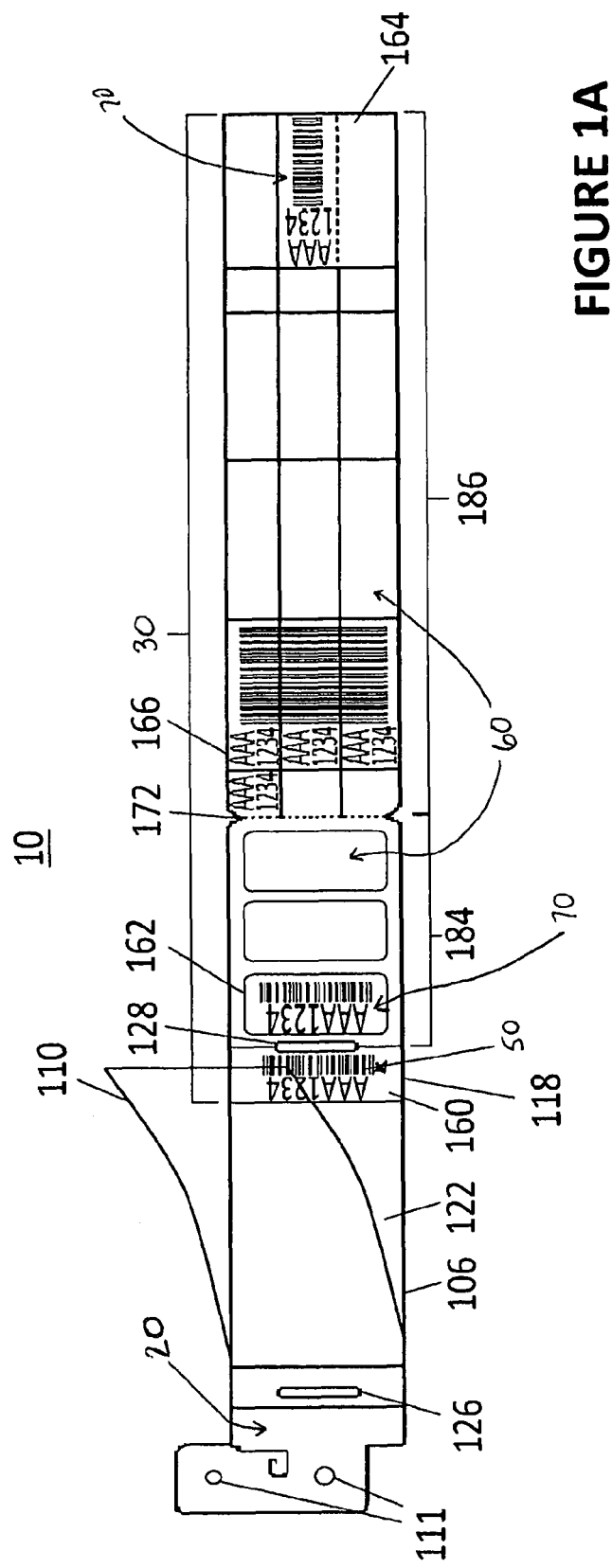
FIG. 1A is a simplified top view of a recipient verification system in accordance with the principles of the present disclosure before application of the system to a recipient.
Figure 1B:
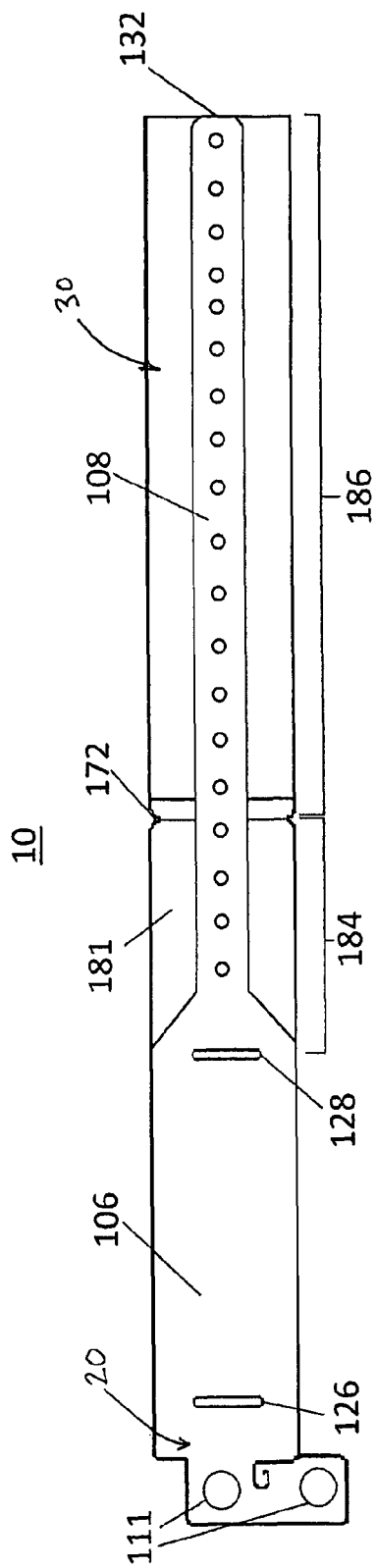
FIG. 1B is a simplified bottom view of the system of FIG. 1A.
Figure 1C:
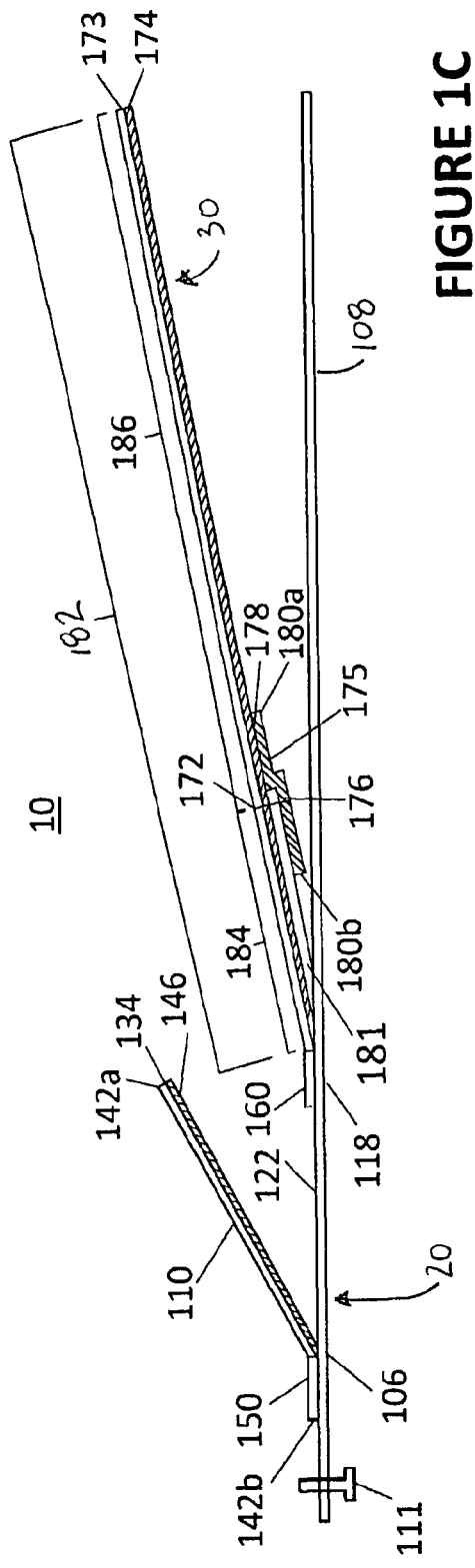
FIG. 1C is a simplified side view of the system of FIG. 1A and illustrates the system layers.

A recipient verification system 10 in accordance with aspects of the present disclosure is shown in FIGS. 1A, 1B, and 1C. As shown in FIG. 1A, the recipient verification system 10 generally includes a band 20 and a label strip 30. As made clear below, the band 20 and the label strip 30 can assume a variety of forms. In some embodiments, the label strip 30 otherwise intended for initial direct connection to the band 20 can be omitted. In more general terms, aspects of the present disclosure relate to a band identifier carried on the band 20 and on one or more labels (that may or may not be provided with the label strip 30). For example, FIG. 1A illustrates a permanent band identifier 50 permanently provided on the band 20 (e.g., when the band 20 is worn by a user, the permanent band identifier 50 cannot be removed from the user without removing the entire band 20). The label strip 30 forms a number of labels 60 (referenced generally) that are intended to be disconnected from the band 20 during use (described below), one or more or all of which display a removable band identifier 70. Alternatively, the system can consist of the band 20 (that otherwise includes or displays the permanent band identifier 50) and one or more of the labels 60 that are never physically connected to the band 20, but still display the removable band identifier 70. In yet other embodiments, the label strip 30 is integrally formed with the band 20. Regardless, the permanent band identifier 50 is always associated with the band 20, and is not provided with the label(s) 60 that are otherwise intended to be disconnected from the band 20 (or are never connected to the band 20). Instead, the removable band identifier 70 is associated with these label(s) 60. The permanent and removable band identifiers 50, 70 are, in many respects, identical. However, the permanent band identifier 50 is configured to include a "hidden" verification code that distinguishes the permanent band identifier 50 from the removable band identifier 70.

Figure 1D:
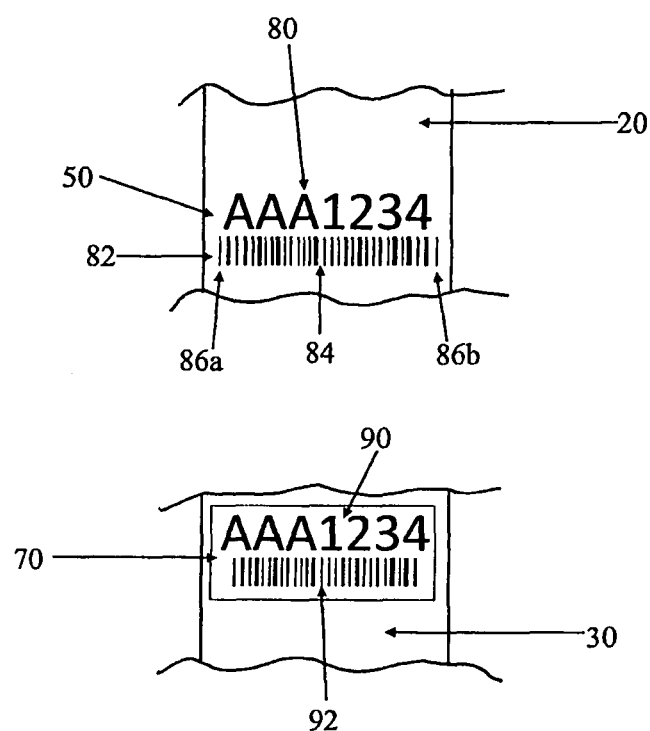
FIG. 1D is a simplified plan view illustrating a comparison of a permanent band identifier and a removable band identifier useful with the system of FIG. 1A.

FIG. 1D illustrates the permanent band identifier 50 and the removable band identifier 70 in greater detail and side-by-side for ease of explanation. The permanent band identifier 50 includes a human readable code 80 and a machine readable code 82. The human readable code 80 represents the exact identification code assigned to the system 10 (FIG. 1A) in human readable form. The machine readable code 82 includes an identification code section 84 and at least one verification code section 86a, 86b. The information embodied by the identification code section 84 is identical to the human readable code 80, but in machine readable format. The verification code section(s) 86a, 86b represent, in machine readable format, information differing from, or in addition to, the identification code information of the identification code section 84. For ease of illustration, the verification code sections 86a, 86b are shown in FIG. 1D as additional barcode-type lines; alternatively, the verification code "sections" can be implemented using check digit-type barcode technology whereby the verification code is "embedded" into the printed barcode. Other symbology architectures are equally acceptable. In some embodiments, the first verification code section 86a represents, in machine readable format, a first letter, number or character (e.g., "S"), and the second check digit section 86b represents, in machine readable format, a second letter, number or character (e.g., "W"). The verification code sections 86a, 86b can alternatively be identical. In other embodiments, only one verification code section is provided; alternatively, three or more verification code sections can be incorporated into the machine readable code 82. When scanned, the machine readable code 82 identifies the same information as the human readable code 80, along with at least one additional item of information. By way of example, the human readable code 80 of FIG. 1D is "AAA1234" and when the machine readable code 82 of FIG. 1D is scanned with an appropriate barcode reader, the machine readable code 82 decodes as "SAAA1234W".

The removable band identifier 70 also includes a human readable code 90 and a machine readable code 92. The human readable code 90 of the removable band identifier 70 is identical to the human readable code 80 of the permanent band identifier 50. The machine readable code 92 of the removable band identifier 70 is highly similar to, but differs from, the machine readable code 82 of the permanent band identifier 50. In particular, the machine readable code 92 represents, in machine readable format, only the identification code information of the human readable code 80, 90. In other words, the machine readable code 92 of the removable band identifier 70 is identical to the identification code section 84 of the machine readable code 82 of the permanent band identifier 50, and does not include any of the verification code sections 86a, 86b. By way of example, when scanned with an appropriate barcode reader, the machine readable code 92 decodes as "AAA1234". The verification code section(s) 86a, 86b are thus akin to check digit symbology techniques employed with barcode printing whereby a human viewer of the machine readable code 82 cannot visually perceive the presence of the verification code section(s) 86a, 86b (when visually comparing the permanent machine readable code 82 with the removable machine readable code 92), but readily distinguishes the scanned permanent machine readable code 82 from the scanned removable machine readable code 92 when decoded.

The machine readable codes 82, 92 can assume a variety of formats. For example, the machine readable codes 82, 92 can be linear barcodes, 2D barcodes, other optically-read coding formats, RFIDs, etc.

With the above construction, a caregiver facility (or other institution utilizing the system 10) can confirm whether desired protocols are followed during use of the system 10. For example, a caregiver can be instructed that for certain patient-related activities, the permanent band identifier 50 must be scanned. In other words, the caregiver is not permitted to associate an action item with a particular patient by scanning only the information provided on a label removed from the patient (e.g., one of the labels 60) that the caregiver can only assume belongs to the patient. Because the human readable codes 80, 90 are identical, the caregiver will not be aware of the fact that the machine readable codes 82, 92 differ slightly. The computer network system employed by the caregiver facility is programmed to effectively "recognize" this difference, parsing the information of the verification code sections 86a, 86b from the identification code information of the identification code section 84. Thus, when the machine readable code 82 of the permanent band identifier 50 is scanned, the computer network system notes and records the identification code information (that has otherwise been assigned to a particular patient) along with verification information (or at least that the verification code characters or information were otherwise present in the scanned data string). Thus, the caregiver facility has information confirming that the permanent band identifier 50, and not the removable band identifier 70, was scanned by the caregiver. Scanned information of the removable band identifier 70 will not include the verification designator(s). In some embodiments, the computer network system is programmed to generate an alert or warning when it is determined that the scanning protocol has not been followed (e.g., when it is determined that the caregiver mistakenly scanned a label displaying the removable band identifier 70 instead of the permanent band identifier 50 under circumstances where the protocol requires scanning of the permanent band identifier 50 (that is otherwise directly connected to the recipient via the band 20).).

With the above explanations of the band identifiers 50, 70 in mind, and returning to FIGS. 1A-1C, in some embodiments the band 20 includes or defines a base 106, a strap 108 (hidden in FIG. 1A, but visible in FIG. 1B), a shield 110, and a closure 111. The label strip 30 extends from the base 106 along (but not attached to) the strap 108 and displays the permanent band identifier 50 on a permanent label 160 that is otherwise permanently fixed to the band 20 as described below. In other embodiments, the permanent band identifier 50 can be permanently associated with the band 20 apart from features of the label strip 30 (e.g., the permanent band identifier can be printed directly on to the band 20). In the embodiment shown in FIG. 1A, the permanent band identifier 50 includes both the human readable code (e.g., alpha-numeric format) 80 and the machine readable code (e.g., barcode format) 82.

The recipient verification system 10 transitions from an initial state, in which the strap 108 shown in FIG. 1B is free of the closure 111, to a worn state in which the strap 108 is wrapped about a recipient's appendage and secured to the base 106 at the closure 111. In the initial or the worn state, the permanent band identifier 50 may be protected by and visible through the shield 110. In some embodiments, the base 106 and the strap 108 are constructed by a material web including a bottom layer adapted for contact with human skin.

As shown in FIG. 1C, the base 106 defines a band identification portion 118. The permanent band identifier 50 (not visible in FIG. 1C, but shown in FIG. 1A) is displayed on the band identification portion 118 by the permanent label 160. In the embodiment shown, the permanent label 160 is a contiguous section of the label strip 30. In alternative embodiments, the permanent label 160 can be a separate label that is non-contiguous with the label strip 30. Alternatively in another embodiment, the permanent band identifier 50 may be applied to the base 106 by direct printing without the use of a label.

In some embodiments, the base 106 also defines an optional recipient information portion 122 sized to receive a recipient information label (e.g., a hospital label). As a point of reference, the recipient information label is absent from FIGS. 1A-1C to better illustrate the recipient information portion 122. In other embodiments, the material of the label strip 30 may be lengthened such that a section of the label strip 30 is coextensive with the base 106 over the recipient information portion 122. In this embodiment, the recipient information label applied to the recipient information portion 122 would be adhered to the surface of the label strip 30 rather than to the surface of the base 106 (with that section of the label strip 30, in turn, being applied over the recipient information portion 122). The recipient information portion 122 may contain prompts that instruct the caregiver to place a recipient information label onto that location. In other embodiments, the recipient information portion 122 can have a shorter length than implicated by the drawings to provide a limited area for the caregiver to apply patient-related information (e.g. patient date-of-birth, etc.).

As shown in FIGS. 1A and 1B, the base 106 optionally further defines first and second passages 126, 128 through a thickness thereof. The first and second passages 126, 128 are formed at opposing sides of the base 106 in a manner not obstructing the permanent band identifier 50. The first and second passages 126, 128 are sized to receive a separate attachment device strap (not shown) in an alternate worn state. In this alternate worn state configuration, the first and second passages 126, 128 function as part of a band replacement feature as described in U.S. application Ser. No. 12/465, 449 filed May 13, 2009 and entitled "Recipient Verification Systems and Methods of use, Including Patient Identification, " the entire teachings of which are incorporated herein by reference. While the passages 126, 128 are illustrated as being closed-ended slots, other configurations are also acceptable (e.g., holes, perforations, slots open to an edge of the base 106, etc.).

The strap 108 shown in FIG. 1B extends from the base 106 and is sized for placement about a recipient's appendage (e.g., wrist or ankle). The strap 108 terminates at a tail end 132 and is adapted for placement about a recipient's wrist, ankle, or other appendage. As a point of reference, FIGS. 1A, 1B, and 1C illustrate the recipient verification system 10 prior to placement about the recipient's appendage.

The closure 111 is used to secure the strap 108 around the recipient's appendage. The closure 111 shown in the embodiment of FIGS. 1A, 1B, 1C, is a snap closure commonly known in the art. In general, the closure 111 is comprised of two mating components designed to engage one another in a single-use, tamper-evident fashion. In alternative embodiments, the closure 111 may be comprised of other various closures commonly known to those skilled in the art, including adhesive closures, hook and loop closures, external clip closures, etc.

As shown in FIG. 1C, the shield 110 is attached to the base 106 and includes a transparent or substantially transparent film layer 134 with an adhesive lining. An optional release liner 146 can be provided with the shield 110 to prevent premature activation or exposure of the adhesive on the shield film layer 134. The shield 110 further defines a leading end 142a and a trailing end 142b. In the initial state (i.e. prior to physical connection of the recipient verification system 10 to a recipient), the leading end 142a is free of the base 106 and can move relative to the base 106. The trailing end 142b is attached to the base 106 at an exposed adhesive area or adhesive attachment area 150. The exposed adhesive area 150 is shown in FIG. 1C as being proximal to the closure 111, but the shield 110 may also be oriented with the exposed adhesive area 150 distal to the closure 111 and proximal to the second passage 128. In this alternate embodiment, the exposed adhesive area 150 on the shield 110 can be utilized as a combination attachment feature for the shield 110 as well as a protective covering for the permanent label 160. Upon final assembly of the recipient verification system 10 to a recipient, the release liner 146 is removed and the leading end 142a of the shield 110 is adhered to the base 106. In some embodiments, the shield 110 is sized to completely cover the recipient information portion 122 and the permanent label 160 while terminating at the second passage 128.

The shield 110 can be made of a clear material that facilitates legibility of the permanent band identifier 50 code and scanning/reading of machine readable code formats or other communication means (e.g., barcode, optically readable code, RFID, etc.). In one embodiment, the shield 110 is a single piece of material attached to the base 106 via the exposed adhesive area 150 as described above. Upon application, the shield 110 in this embodiment simultaneously protects both the recipient information portion 122 and the permanent label 160. In embodiments where the permanent label 160 is sufficiently durable, the shield 110 may be sized to cover or protect only the recipient information portion 122.

In further embodiments, the shield 110 may be comprised of two separate pieces to separately protect the recipient information area 122 and the permanent label 160. In these constructions, each piece of the shield 110 has its own adhesive attachment area 150. In alternate embodiments, the adhesive attachment area 150 that attaches the shield 110 to the base 106 can be replaced with an ultrasonic weld, solvent bond, or other attachment means. In other embodiments, the shield 110 has points or lines of weakness at its leading end 142a to promote tamper evidence if the shield 110 is removed after application.

The band 20 can be formed and assembled in a variety of manners. In some embodiments, the band 20 is initially defined as a die-cut, single or multi-layer laminate structure, formed apart from the label strip 30 (i.e., the band 20 and the label strip 30 are not commonly defined in a single contiguous form-like structure). The strap 108 is integrally formed with the base 106 such that the base 106 and the strap 108 form a contiguous, homogeneous body. The laminate material(s) are selected to be flexible, resistant to tearing, durable, acceptable for contact with human skin, and take into account patient comfort. For example, acceptable laminate material(s) include polyethylene, polyester, vinyl, nonwoven foams, low-density polyethylene/COC blends, Tyvek™, etc. Alternatively, the base 106 and the strap 108 can be formed of differing materials. For example, the strap 108 can be Tyvek™ to allow for comfort, while the base 106 can be polyethylene to provide a more structured support for the label strip 30.

As shown in FIG. 1A, the label strip 30 is composed of the plurality of labels 60 generally mentioned above and the permanent label 160. The plurality of labels 60 can include one or more of a plurality of removable labels 162, a test tube label 164, a plurality of detachable labels 166, and an adhesive strip 176. The size, shape, and/or number of the removable labels 162, test tube label 164, and detachable labels 166 can vary as desired; however, at least one removable label 162 (apart from the permanent label 160) is provided with the label strip 30. The removable band identifier 70 is identically displayed (e.g., printed) by at least one removable label 162, at least one of the detachable labels 166, and the test tube label 164; in some embodiments, the removable band identifier 70 is displayed by every discrete label 60 defined by the label strip 30 apart from the permanent label 160 (that otherwise displays the permanent band identifier 50 in some embodiments). In one embodiment, the label strip 30 is printed onto one continuous backing comprising a facestock layer 173 and a liner layer 174 as shown in FIG. 1C. Additional liner layers, such as layer 181, may be added to sections of the label strip 30 as needed to enhance system 10 durability. In yet other embodiments, the permanent label 160 is formed apart from and can be spaced apart from the label strip 30.

The label strip 30 can be formed separately from the band 20. In some embodiments, the label strip 30 is subsequently adhered to the base 106 by application and permanent bonding of the permanent label 160 to the band identification portion 118. In general, the remaining portions (identified at 182 in FIG. 1C) of the label strip 30 may move independently of the band strap 108. This independence allows the band strap 108 to be sized and secured around a patient while allowing the label strip 30 to remain secured to the base 106 and fully intact. This attachment of the label strip 30 to the base 106 of the band 20 creates a physical link between the two components 20, 30 and minimizes the likelihood that either component will be separated and misplaced during band application. In alternative embodiments, the label strip 30 may be positioned on various other locations along the band 20. The location of the label strip 30 relative to the band 20 is not limited by what is described herein. The present disclosure is not limited to embodiments in which the band 20 and the label strip 30 are separately formed and subsequently assembled; in yet other embodiments, the band 20 and the label strip 30 are integrally formed as a homogeneous structure. In general, free portion 182 of the label strip 30 may be divided into two regions by a line or area of weakness 172: a removable label region 184 and a detachable label region 186. The functions of each region 184, 186 are detailed in later paragraphs.

FIG. 1C shows the adhesive strip 176 beneath both the removable label region 184 and the detachable label region 186. The adhesive strip 176 contains an adhesive layer 178 covered by a liner 175. In one embodiment, the adhesive strip 176 is placed across the area of weakness 172 between the both removable label region 184 and the detachable label region 186. The area of weakness 172 divides the adhesive strip 176 into a leading segment 180a and a trailing segment 180b. In alternative embodiments, the adhesive strip 176 may be composed of two independent adhesive strips, one positioned beneath the removable label region 184 and another positioned beneath the detachable label region 186. In general, a width of the adhesive strip 176 is equal to or less than a width of the label strip 30. Optionally, a width of the adhesive strip 176 along at least the trailing segment 180b approximates or is slightly smaller than a width of the strap 108. In another embodiment, the removable label region 184 may be secured to the band 20 without the use of an adhesive strip 176. In this embodiment, an additional passage similar to passages 126, 128 may be provided in the removable label region 184 and sized to receive the strap 108 prior to securing the strap 108 at the closure 111.

The removable labels 162 are positioned or formed on or by the label strip 30 in a section noted as the removable label region 184. Because this region 184 is a section of the label strip 30, the region 184 may move independently of the band strap 108 prior to application of the band 20 to a recipient as described above. By allowing this independent motion of the removable label region 184, obstruction of the strap 108 by the region 184 is avoided during band application. Once the strap 108 is secured to the closure 111 during band application, the removable label region 184 may be secured to the strap 108 by removing the adhesive liner 175 from the trailing segment 180b of the adhesive strip 176 and effectuating a bond between the thusly exposed adhesive and the strap 108. Notably, the leading segment 180a may continue to be covered by a remaining portion of the liner 175. By securing the removable label region 184 to the strap 108 in the worn state, the removable labels 162 are more robustly connected to the band 20 and more readily remain with the band 20 while it is worn by the recipient.

In some embodiments, the removable labels 162 are configured such that the label perimeter is not adjacent to the border of the removable label region 184. That is to say, while a width of the removable label region 184 may or may not be the same as the width of the band base 106, a perimeter of each individual removable label 162 (for example as conventionally cut into the facestock layer 173 of the label strip 30) terminates interior of the base 106 width or border. This configuration can render the removable labels 162 much more resistant to falling off while the system 10 is worn on a recipient (during showers, etc.).

The detachable labels 166 are positioned or formed on or by the label strip 30 in a section noted as the detachable label region 186. During use, the detachable label region 186 is first detached along the area of weakness 172 after attachment of the band 20 to the recipient. The detachable label region 186 can then be adhered to various articles (e.g. specimen tubes, etc.) by removing the adhesive liner 175 beneath the leading end 180a of the adhesive strip 176.

It is desirable that the permanent label 160, removable labels 162, test tube label 164, and detachable labels 166 are virtually identical in their markings to ensure patient safety (apart from the differences described above with respect to differences between the machine readable code 82 of the permanent band identifier 50 displayed on the permanent label 160 and the machine readable code 92 displayed on the remaining labels 60). Removable labels 162 and detachable labels 166 can be provided in any quantity or format (e.g. machine-readable, human-readable) desired by the user. In one embodiment shown in FIG. 1A, the detachable labels 166 may contain machine readable codes (e.g. barcodes) that span several labels and are divided by the border of each discrete detachable label 166.

The band identifiers 50, 70 displayed on the label strip 30 are created on a variable basis by a manufacturer of the recipient verification system 10 (as opposed to a caregiver institution user of the recipient verification system 10 or the recipient). The band identifiers 50, 70 can be indicia in one or more formats or configurations depending on the situation and process needs. For example, in some exemplary embodiments, the band identifiers 50, 70 includes the unique band code that is generated in one or more forms such as alphanumeric, barcode, magnetic stripe, RFID, etc. Alternatively, the band identifiers 50, 70 indicia can assume other forms (such as prompts, instructions, icons, etc.) or be omitted. The recipient verification system 10 can contain colors, icons, or other means that aid caregivers and patients in identifying the purpose/intent of the recipient verification system 10.

A different, predetermined band identifier code can be created for each new recipient verification system 10 supplied to an institution. In practice, the institution optionally maintains an electronic database (or written record) that assigns the predetermined band identifier code to a particular recipient to whom the recipient verification system 10 is applied. Subsequently, that same, predetermined band identifier code is then correlated in the database with relevant recipient information. For example, the recipient can be a patient admitted to a hospital and submitting test specimen(s) at a laboratory.

In general, the process for the application and use of the recipient verification system 10 can proceed as follows. First, any hospital label, card, tab, or other carrier mechanism will be transcribed with desired information, for example recipient, caregiver, and/or other hospital related information. The resultant recipient information label, which can come in any format or material per the specific hospital's procedure, is placed in, and bonded to, the recipient information portion 122. The shield 110 is then sealed down over the so-applied recipient information label and the permanent label 160 by first removing the release liner 146 and then sealing the shield 110 to the base 106. This provides protection to the applied recipient information label and the permanent label 160.

The recipient verification system 10 is connected to a recipient by wrapping the strap 108 about the recipient's appendage and securing the band closure 111. Once the recipient verification system 10 is attached to the recipient, the remaining length of the strap 108 can be stored by inserting it into the first passage 126. In other embodiments, the excess strap 108 material can be removed (if desired) using a scissor or equivalent means.

Once the recipient verification system 10 is attached to the recipient, the test tube label 164 can be removed and placed on any number of specimen carrying vehicles. Then, the detachable label region 186 can be removed at the area of weakness 172. The detachable label region 186 travels with the specimen (or specimen carrying vehicles), and the detachable labels 166 can be attached to the specimen or any paperwork, etc., via the adhesive strip 176 leading segment 180a (that otherwise remains with the detachable label region 186 upon detachment of the detachable region 186 from the removable label region 184). In some embodiments, the leading segment 180a of the adhesive strip 176 is attached to the recipient sample tube prior to applying the recipient verification system 10 to the patient and/or drawing the patient sample.

The removable labels 162 remain with the recipient in case they are needed to label anything related to the recipient (another specimen, paperwork, etc.) at a later time. The permanent label 160, removable labels 162, test tube label 164, and detachable labels 166 all embody the same predetermined band identifier code. Subsequently, when the labels 162-166 are placed on any specimen, order form, paperwork, drugs, organs, tissues, or blood being delivered to the recipient, the labels 162-166 can be compared against the permanent band identifier 50 on the permanent label 160 to enable recipient verification.

The recipient information label (e.g., hospital label or other applied information) secured to the recipient information portion 122 can be accessed for further recipient identification by comparing applied information on the recipient information label to medical records, for instance. In some embodiments, the permanent band identifier 50 on the permanent label 160 is read and/or used to ensure proper delivery of recipient intended products using a bedside scanning device as described above. Additionally, a printer system and label stock can be used to make more of the detachable labels 166 at the point of use as needed.

Figure 2A:
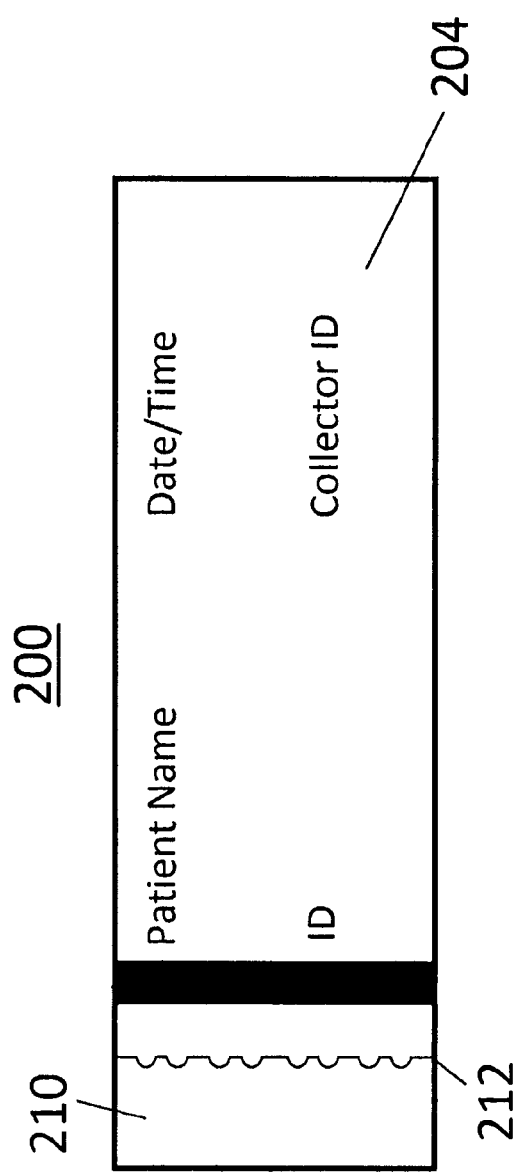
FIG. 2A is a simplified top view of the write-on label construction supplemental component useful with systems of the present disclosure.
Figure 2B:
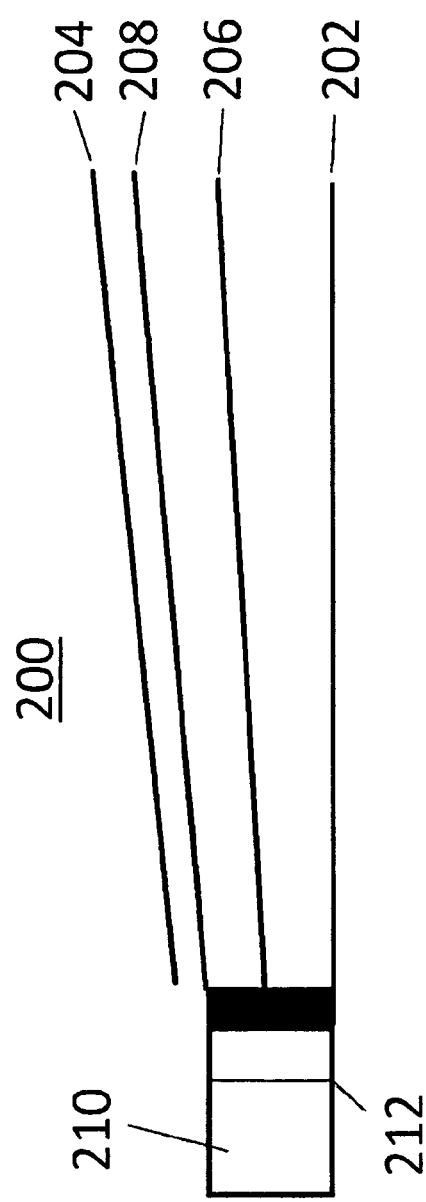
FIG. 2B is a side view of the write-on label construction supplemental component of FIG. 2A.

In some institutions or applications, preprinted hospital labels are not available, and/or handwritten label formats are preferred. Under these circumstances, the recipient information portion 122 can be formatted to be ink-receptive for receiving hand-written information. It is desirable to avoid transcription errors and ensure that the information on the patient-attached portion of the recipient verification system 10 is identical to that on the specimen or other recipient related vehicle. FIGS. 2A and 2B show top and side views of a write-on label construction 200 useful for achieving these requirements. The write-on label construction 200 may be used as a supplemental component of the recipient verification system 10 shown in FIGS. 1A-1C.

During manufacturing, the write-on label construction 200 may be adhered over the recipient information portion 122. A label/face stock layer 204 displays prompts that suggest desirable information that can be written on to the label/face stock layer 204 using, for example, a ballpoint pen. Desired information is written onto the label/face stock layer 204 and is transferred via image transfer paper, carbon paper or similar material layer(s) 206 to the desired surface. The label layer 204 that is intended for the recipient specimen or other recipient-related items is removed from a corresponding release liner 208 and applied as desired. In some embodiments, a liner layer 202 may protect image material carried by the write-on label construction 200 from premature transfer. The liner layer 202 is removed prior to writing. In some embodiments, the liner layer 202, label/face stock layer 204 and the image transfer paper layer 206 are attached to one another for convenience of use by a connector piece 210. Layers such as the liner layer 208 can be removed via a weakened area 212 located between the layers 202-208 and the connector 210. This information write-on label construction 200 can stand alone, or be attached to the recipient information portion 122 in a variety of ways, including during the initial manufacturing of the recipient verification system 100. In some embodiments (not shown), the label/face stock layer 204 may be printed to include the removable band identifier 70 (FIG. 1D) or the band identifier 70 can be added as an additional label covering a portion of the label/face stock layer 204. In yet other embodiments, the band identifier 70 can be embedded into the write-on label construction 200 in the form of an alternate machine readable format such as RFID.

In other embodiments, the band 20 (FIGS. 1A-1C) may be comprised of some or all of the layers 202-208 shown on the write-on label construction 200. By using the same layers between the write-on label construction 200 and the band 20, the manufacturing of the subsequent recipient verification system 10 would be simplified. In alternative embodiments, the layers 202-208 of the write-on label construction 200 may comprise only a section of the band 20 rather than the whole band.

In further embodiments, the label strip 30 (FIGS. 1A-1C) may also be comprised of some or all the layers 202-208 shown on the write-on label construction 200. In these embodiments, some or all of the layers 202-208 could extend into the recipient information portion 122 and be configured to receive patient-related information.

Returning to FIGS. 1A-1C, in yet other embodiments, the band 20 can be configured to eliminate the recipient information portion 122. With this "condensed" version of the system 10, no information apart from the permanent band identifier 50 is supplied or provided directly on the band 20.

As will be evidenced by the above explanations, the present disclosure is not limited to any particular band or label strip format. Any band or label strip configuration is acceptable in conjunction with the permanent band identifier and removable band identifier features described above.

The recipient verification systems, methods of manufacture, and methods of use of the present disclosure provide marked improvements over previous designs. Caregiver facilities are provided with the ability to confirm that required protocols are followed when scanning machine readable information in connection with a patient-related activity. Optionally, and in contrast to conventional "all-in-one" or form-based systems in which the band and the label strip are simultaneously formed from the same stock material sheet, by forming the band and the label strip as separate components, the systems of the present disclosure permit the use of desired materials for each discrete component (e.g., the material use for the band can be strong, tamper evident and durable, while the material used for the label strip can be soft, easy to process and print on). With embodiments in which the label strip and the band are not coextensive (e.g., the two components do not fully overlap), the label strip is secured to the band in a small section and the remaining portion of the label strip hangs freely. This independence between the label strip and the band allows the band strap to be more easily sized and secured to the recipient while the label strip is still physically linked to the band.

Although the present disclosure has been described with reference to preferred embodiments, workers skilled in the art will recognize that changes can be made in form and detail without departing from the spirit and scope of the present disclosure.

What is claimed is:

1. A recipient verification system comprising:
    a band including:
        a permanent band identifier,
        a strap; and
    at least one label displaying a removable band identifier;
    wherein:
        the permanent band identifier and the removable band identifier include an identical human readable code,
        the removable band identifier includes a machine readable code embodying information identical to the human readable code,
        the permanent band identifier includes a machine readable code embodying information identical to the human readable code and a verification code;
    and further wherein the information embodied by the machine readable code of the removable band identifier does not include the verification code and thus differs from the machine readable code of the permanent band identifier such that upon performance of a scanning operation in which the machine readable code of only one of the permanent band identifier and the removable band identifier is scanned and then decoded, presence or absence of the verification code in the decoded machine readable code confirms whether the permanent band identifier or the removable band identifier was scanned.

2. The recipient verification system of claim 1, wherein the machine readable code of the permanent band identifier includes an identification code section and at least one verification code section, and further wherein the identification code section represents, in machine readable format, information identical to the human readable code.

3. The recipient verification system of claim 2, wherein the at least one verification code section represents, in machine readable format, at least one of a letter, number or character.

4. The recipient verification system of claim 2, wherein the machine readable code of the permanent band identifier includes first and second verification code sections.

5. The recipient verification system of claim 4, wherein the machine readable code of the permanent band identifier comprises, in order, the first verification code section, followed by the identification code section, followed by the second verification code section.

6. The recipient verification system of claim 2, wherein the machine readable code of the removable band identifier does not include the at least one verification code section.

7. The recipient verification system of claim 1, wherein the permanent band identifier is permanently affixed to the band and the removable band identifier is permanently affixed to the at least one label.

8. The recipient verification system of claim 1, wherein the band further includes a base extending from the strap, and further wherein the permanent band identifier is displayed along the base.

9. The recipient verification system of claim 8, wherein the band further forms first and second passages through a thickness of the base, and further wherein the permanent band identifier is located between the first and second passages.

10. The recipient verification system of claim 9, wherein the first and second passages are configured to receive a replacement strap.

11. The recipient verification system of claim 8, wherein the base defines a band identification portion, and further wherein the permanent band identifier is displayed on the band identification portion.

12. The recipient verification system of claim 11, wherein the permanent band identifier is printed on to the band identification portion.

13. The recipient verification system of claim 11, wherein the permanent band identifier is formed on a label bonded to the band identification portion.

14. The recipient verification system of claim 1, further comprising:
a label strip including the at least one label.

15. The recipient verification system of claim 14, wherein the label strip is formed apart from the band.

16. The recipient verification system of claim 15, wherein the label strip further includes a permanent label in addition to the at least one label, and further wherein the permanent label is configured for permanent affixment to the band and displays the permanent band identifier.

17. The recipient verification system of claim 16, wherein the at least one label includes a removable label, a test tube label, and a detachable label, and further wherein each of the removable label, the test tube label and the detachable label displays the removable band identifier and does not display the permanent band identifier.

18. A method of confirming adherence to an activity protocol with a desired recipient, the method comprising:

associating a recipient verification system with the desired recipient, the recipient verification system including a band and at least one label, wherein the band includes a permanent band identifier and the at least one label displays a removable band identifier, wherein the permanent band identifier differs and the removable band identifier include an identical human readable code, and even further wherein the permanent band identifier includes a machine readable code comprising a verification code and even further wherein the removable band identifier includes a machine readable code that does not comprise the verification code and differs from the machine readable code of the permanent band identifier;

receiving and decoding scanned information from a caregiver intending to perform an activity for the desired recipient;

determining whether the decoded information correlates with the permanent band identifier or the removable band identifier based upon an identification of a presence or absence of the verification code in the decoded information; and evaluating adherence to the activity protocol based upon the determination.

19. The method of claim 18, wherein the step of determining includes reviewing the scanned information for presence of the verification code.

20. The method of claim 18, wherein the step of associating includes:

receiving the recipient verification system in an initial state that consists of the band and a label strip including the at least one label and a permanent label displaying the permanent band identifier;

permanently bonding the permanent label to a base of the band;

wrapping the strap about an appendage of the desired recipient; and securing the strap to the base to directly associate the band to the desired recipient.

* * * * *